(12) United States Patent
Ohta (10) Patent No.: US 11,358,110 B2
(45) Date of Patent: Jun. 14, 2022

(54) INTERNAL, FLUIDIZED BED REACTION APPARATUS, AND METHOD FOR MANUFACTURING TRIFLUOROMETHYL PYRIDINE-BASED COMPOUND

(71) Applicant: ISHIHARA SANGYO KAISHA, LTD., Osaka (JP)

(72) Inventor: Hiroyuki Ohta, Osaka (JP)

(73) Assignee: ISHIHARA SANGYO KAISHA, LTD., Osaka (JP)

(*) Notice: Subject to any disclaimer, the term of this patent is extended or adjusted under 35 U.S.C. 154(b) by 0 days.

(21) Appl. No.: 17/049,387

(22) PCT Filed: Apr. 22, 2019

(86) PCT No.: PCT/JP2019/016981
§ 371 (c)(1),
(2) Date: Oct. 21, 2020

(87) PCT Pub. No.: WO2019/208482
PCT Pub. Date: Oct. 31, 2019

(65) Prior Publication Data
US 2021/0060510 A1    Mar. 4, 2021

(30) Foreign Application Priority Data

Apr. 23, 2018 (JP) .............................. JP2018-082539

(51) Int. Cl.
*B01J 8/00* (2006.01)
*B01J 8/18* (2006.01)
(Continued)

(52) U.S. Cl.
CPC ............... *B01J 8/34* (2013.01); *B01J 8/1872* (2013.01); *C07D 213/61* (2013.01)

(58) Field of Classification Search
CPC ..... B01J 8/00; B01J 8/18; B01J 8/1836; B01J 8/1872; B01J 8/24; B01J 8/34;
(Continued)

(56) References Cited

U.S. PATENT DOCUMENTS 2,314,836 A * 3/1943 Seil ........................... F27B 7/16
432/117
2,769,771 A * 11/1956 Griffin, Jr. ................. B01J 8/34
208/163
(Continued)

FOREIGN PATENT DOCUMENTS

CN    2305244 Y    1/1999
CN    2305245 Y    1/1999
(Continued)

OTHER PUBLICATIONS

International Search Report from PCT Application No. PCT/JP2019/016981 dated Jul. 23, 2019.
(Continued)

*Primary Examiner* — Natasha E Young
(74) *Attorney, Agent, or Firm* — Harness Dickey & Pierce P.L.C.

(57) ABSTRACT

An aspect of the present invention provides an internal and the like. The internal is easily handled and is capable of yielding a satisfactory defoaming effect. An internal (50) is used in a fluidized bed reaction device (1), in which a first material and a second material are brought into contact with each other and reacted with each other. The internal (50) is attached to a ceiling part of the fluidized bed reaction device (1), and includes a plurality of chains (21).

7 Claims, 4 Drawing Sheets

(51) Int. Cl.
*B01J 8/24* (2006.01)
*B01J 8/34* (2006.01)
*B01J 19/00* (2006.01)
*B01J 19/24* (2006.01)
*C07B 61/00* (2006.01)
*C07D 213/61* (2006.01)

(58) Field of Classification Search
CPC ...... B01J 19/00; B01J 19/0053; B01J 19/006; B01J 19/24; B01J 2219/00; B01J 2219/00761; B01J 2219/00763; B01J 2219/00765; B01J 2219/00768; B01J 2219/24; C07B 61/00; C07D 213/00; C07D 213/02; C07D 213/04; C07D 213/60; C07D 213/61
See application file for complete search history.

(56) References Cited

U.S. PATENT DOCUMENTS

| | | | |
|---|---|---|---|
| 3,989,481 A | 11/1976 | Kunii et al. | |
| 6,265,526 B1 | 7/2001 | Komiya et al. | |
| 2008/0249200 A1 | 10/2008 | Yokoyama et al. | |
| 2009/0104104 A1 | 4/2009 | Inaba | |
| 2010/0074823 A1 | 3/2010 | Inaba | |

FOREIGN PATENT DOCUMENTS

| | | | |
|---|---|---|---|
| CN | 102718699 A | | 10/2012 |
| CN | 105013517 A | | 11/2015 |
| JP | S49131201 A | | 12/1974 |
| JP | S57120084 A | | 7/1982 |
| JP | S5810569 A | | 1/1983 |
| JP | S59104078 A | | 6/1984 |
| JP | H4110406 A | | 4/1992 |
| JP | 2003275572 A | | 9/2003 |
| JP | 2003320338 A | | 11/2003 |
| JP | 3947841 B2 | | 7/2007 |
| JP | 4152114 B2 | | 9/2008 |
| JP | 2009120467 A | * | 6/2009 |
| JP | 2009120467 A | | 6/2009 |

OTHER PUBLICATIONS

International Preliminary Report on Patentability from PCT Application No. PCT/JP2019/016981 dated Oct. 27, 2020.
CA Office Action from corresponding IN Application No. 202017047842 dated Nov. 1, 2021.
Office Action from corresponding Chinese Application No. 2019800273230 dated Dec. 3, 2021.
Partial Supplementary European Search Report from corresponding European Application No. 19793205.6 dated Dec. 15, 2021.

* cited by examiner

INTERNAL, FLUIDIZED BED REACTION APPARATUS, AND METHOD FOR MANUFACTURING TRIFLUOROMETHYL PYRIDINE-BASED COMPOUND

PRIORITY STATEMENT

This application is a national stage application under 35 U.S.C. § 371 of PCT International Application No. PCT/JP2019/016981, published as WO 2019/208482, which has an international filing date of 22 Apr. 2019 and claims priority under 35 U.S.C. § 119 to Japanese Patent Application No. 2018-082539 filed on 23 Apr. 2018. The contents of each application recited above are incorporated herein by reference in their entirety.

TECHNICAL FIELD

The present invention relates to an internal for use in a fluidized bed reaction device in which a first material and a second material different from the first material are brought into contact with each other and reacted with each other. The present invention also relates to a fluidized bed reaction device including the internal, and to a method of producing a trifluoromethyl pyridine-based compound using the fluidized bed reaction device.

BACKGROUND ART

Conventionally, it is known that an internal is used in a fluidized bed reaction device. The internal is a structure which is attached inside the fluidized bed reaction device or with which the fluidized bed reaction device is filled so that a fluidized bed will be kept in a good fluidized condition. Patent Literature 1 discloses an example of such an internal.

CITATION LIST

Patent Literature

[Patent Literature 1]
Japanese Patent Application Publication, Tokukaishou, No. 59-104078 (Publication Date: Jun. 15, 1984)

SUMMARY OF INVENTION

Technical Problem

Internals may have various structures and may be made of various materials. For example, Patent Literature 1 discloses, in FIG. 2, a structure provided with bar-like vertical pieces 12 and crossbars 13 which are made of the same material as the bar-like vertical pieces 12. The bar-like vertical pieces 12 and crossbars 13 are provided at appropriate intervals in the structure. Patent Literature 1 also discloses, in FIG. 3, an internal which is obtained by assembling a plurality of bars into a lattice-like structure.

These internals, which are disclosed in Patent Literature 1, are each a relatively large structure which is deployed throughout the inside of the fluidized bed reaction device. Therefore, it is difficult to attach/detach such an internal to/from a reactor 1. Further, it is not clear how much bubble growth-suppressing effect and defoaming effect the internals have.

The present invention is attained in view of the above problems. An object of the present invention is to provide an internal which is easily handled and which can yield a satisfactory defoaming effect, a fluidized bed reaction device including the internal, and a method of producing a trifluoromethyl pyridine-based compound by use of the fluidized bed reaction device.

Solution to Problem

In order to solve the above problems, an internal in accordance with an aspect of the present invention is an internal for use in a fluidized bed reaction device in which a first material and a second material different from the first material are brought into contact with each other and reacted with each other, the internal including a plurality of chains and being attached to a ceiling part of the fluidized bed reaction device.

With the above configuration, the internal includes a plurality of chains. Since chains are easy to handle, the internal is easily handled. Further, the internal is attached to the ceiling part of the fluidized bed reaction device. The ceiling part is a place where workers can easily work. This makes handling of the internal (in particular, replacement work etc.) easier. Furthermore, in a case where chains are used as at least a part of the internal, it is possible to obtain a defoaming effect, in addition to improved contacting efficiency between the first material and the second material and facilitated circulation of the second material inside the reaction device. Therefore, the above configuration can provide an internal which is easily handled and which makes it possible to obtain a satisfactory defoaming effect.

In order to solve the above problems, a fluidized bed reaction device in accordance with an aspect of the present invention is a fluidized bed reaction device which includes: a body filled with a second material; one or more inlet tubes for introducing, into the body, a first material which chemically reacts with the second material when brought into contact with the second material; and an internal including one or more chains which are hung inside the body.

The above configuration yields the same effect as the internal described above.

Advantageous Effects of Invention

An aspect of the present invention makes it possible to provide an internal which is easily handled and which can yield a satisfactory defoaming effect, a fluidized bed reaction device including the internal, and a method of producing a trifluoromethyl pyridine-based compound by use of the fluidized bed reaction device.

BRIEF DESCRIPTION OF DRAWINGS

FIG. 3(*a*) is a view illustrating an example of an internal in accordance with an embodiment of the present invention.

FIG. 3(*b*) is a view illustrating an example arrangement of a plurality of chains when the cover is viewed from above.

FIG. 4(*a*) is a view illustrating an internal in which chains are connected to each other at a second end.

FIG. 4(*b*) is a view illustrating an internal in which chains are connected to each other at a first end.

DESCRIPTION OF EMBODIMENTS

[Fluidized Bed Reaction Device]

Figure 2:
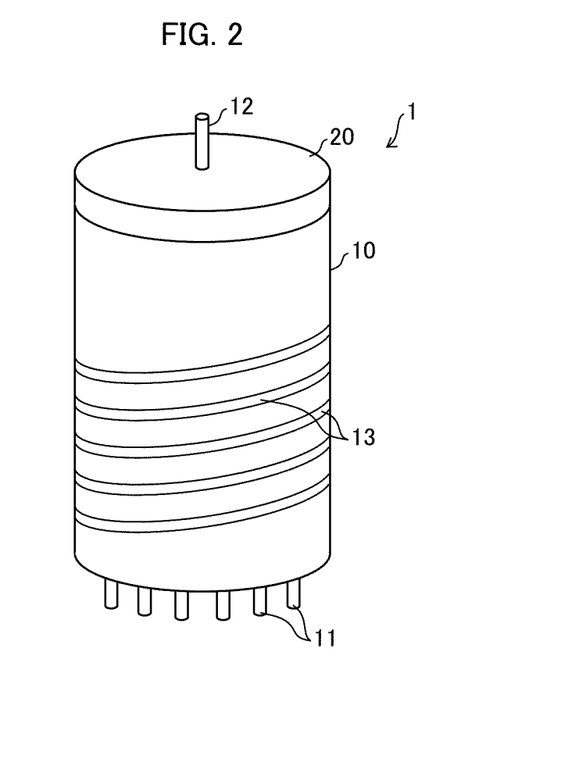
FIG. 2 is a view illustrating a main part of a fluidized bed reaction device in accordance with an embodiment of the present invention.

The following will discuss an example of a fluidized bed reaction device in accordance with an embodiment of the present invention, with reference to FIG. 2. FIG. 2 is a view illustrating a main part of a fluidized bed reaction device 1 in accordance with the present embodiment. For convenience of explanation, hereinafter, in the fluidized bed reaction device 1, a side where a cover 20 is provided is referred to as an "upper direction", whereas a bottom side is referred to as a "lower direction".

The fluidized bed reaction device 1 is used for a chemical reaction which is caused by bringing raw materials (first material) into contact with a catalyst (second material). The following will discuss, as an example, a case in which the fluidized bed reaction device 1 is used for a gas phase reaction in which raw materials and a resultant product of the chemical reaction are both gas. However, the fluidized bed reaction device 1 is also suitably used for causing a chemical reaction other than a gas phase reaction.

The fluidized bed reaction device 1 includes a body 10 and the cover 20. The body 10 forms a space where a catalytic bed (fluidized bed) is formed by filling the space with the catalyst. The body 10 is not particularly limited in shape, size, or material. The present embodiment assumes, as an example, that the main body 10 is a cylindrical tank.

In the present embodiment, the catalyst is solid. More specifically, the catalyst is a particulate catalyst having a small particle size, such as a metal powder.

The body 10 has a bottom provided with one or more inlet tubes 11. The inlet tubes 11 are each a pipe for introducing a gas, which is a raw material (raw material gas), and are connected to the bottom of the body 10. The catalyst flows inside the body 10 as an inflow rate of the raw material gas increases. The present embodiment discusses, as an example, a case where the body 10 includes a plurality of inlet tubes 11. However, the body 10 may include only one inlet tube 11. The inlet tubes 11 are not particularly limited in shape, size, position, or material.

At least one of the inlet tubes 11 may have a tip portion which projects into the body 10 and which has an opening facing the bottom of the body 10. The at least one of the inlet tubes 11, which is configured to have such a shape, makes it possible to reduce the size of gas bubbles (make the gas bubbles fine) which are generated at the time when the raw material gas is introduced. When the body 10 includes the plurality of inlet tubes 11, different types of raw material gases may be introduced into the body 10 from the plurality of inlet tubes 11, respectively.

The body 10 may be provided with a heater 13 inside or outside the body 10. The heater 13 is configured to heat the body 10. The heater 13 can be, for example, a sheathed heater or the like.

The cover 20 is a cover for sealing the body 10. The cover 20 serves as a ceiling part of the body 10. When the cover 20 is closed, an inner side (lower surface) of the cover 20 becomes a ceiling surface of the body 10. The cover 20 is detachably attached to the body 10. It is possible to detachably attach an internal (which will be described below) to the inner side of the cover. The cover 20 is not particularly limited in shape, size, or material.

The cover 20 includes an outlet tube 12. The outlet tube 12 is a pipe for collecting a gas which has been generated by the gas phase reaction. The present embodiment will discuss, as an example, a case where the cover 20 is provided with a single outlet tube 12. However, the cover 20 may include a plurality of outlet tubes 12. The outlet tube(s) 12 is/are not particularly limited in shape, size, position, or material.

[Internal]

Figure 3A:
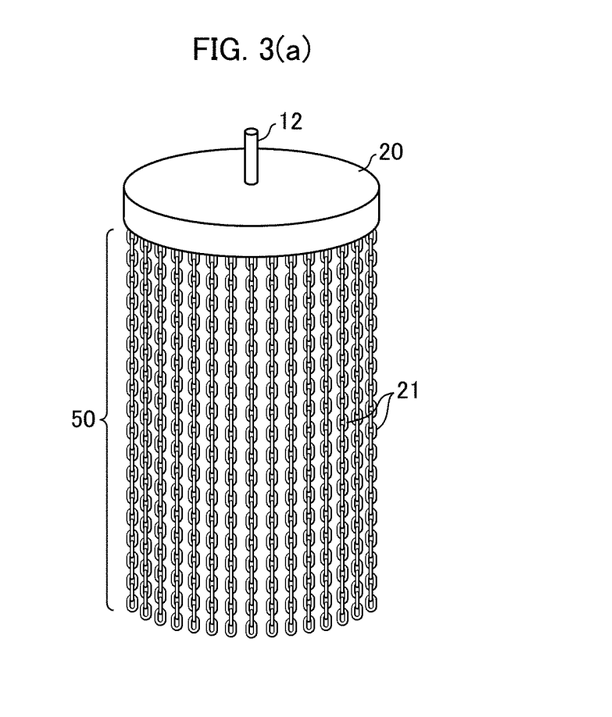

The internal is attached to the inner side of the cover 20. The internal in accordance with the present embodiment will be described with reference to FIG. 3(a). FIG. 3(a) is a view illustrating an example of an internal 50. In FIG. 3(a), the internal 50 is attached to the cover 20.

The internal 50 includes a plurality of chains 21. The number of chains 21 included in one internal 50 is not particularly limited. Each one of the chains 21 is not particularly limited in length, thickness, or shape. Each part constituting the chains 21 is also not particularly limited in shape, size, or material.

The following three effects (1) to (3) can be obtained by using the chains 21 as at least a part of the internal 50. Therefore, the above-described configuration can provide an internal which is easily handled and which makes it possible to obtain a satisfactory defoaming effect.

(1) Improved contacting efficiency between a raw material gas and a catalyst.

(2) Facilitated circulation of the catalyst inside the reaction device.

(3) A bubble growth-suppressing effect and a defoaming effect.

In a case where the fluidized bed reaction device 1 is long and large, the internal 50 and the chains 21 may also become long and large. However, the chains 21 can be bundled or folded as appropriate. Therefore, in a case where the internal 50 becomes long and large, the internal 50, which uses the chains 21, has an advantage of being much more easily handled as compared to an internal which uses another material(s).

Further, it is possible to allow the internal 50 to be easily handled, by attaching the internal 50 on the inner side of the cover 20, that is, to the ceiling part of the fluidized bed reaction device 1. This is because in a case where the internal 50 is attached to the cover 20, there is no need to remove contents (such as the catalyst) inside the fluidized bed reaction device 1 even in a case where the internal 50 needs to be replaced.

Conventionally, a small filling such as Raschig rings or McMahon has been used, as an internal, to fill a fluidized bed reaction device. Such a filling had to be replaced at predetermined times, such as when the filling was corroded in the fluidized bed reaction device. Then, it was necessary to remove a material(s) (e.g., a catalyst) in the reaction device together with the filling, when the filling was replaced.

In contrast, in the case of the internal 50 in accordance with the present embodiment, it is not necessary to remove the contents inside the fluidized bed reaction device 1 at the time of replacement of the internal 50, as described above. Therefore, the internal 50 in accordance with the present embodiment can significantly reduce labor of a worker who replaces the internal 50, a time required for replacement of the internal 50, and the like at the time of replacement of the internal 50, as compared to a case where conventional Raschig rings, McMahon, or the like are used as the internal. This is a superior effect yielded by the internal 50.

The number, length, and thickness of the chains 21 described above may be appropriately determined depending on the size and the shape of each part of the fluidized bed reaction device 1, a material property and a particle diameter of the catalyst (in a case where the catalyst is solid), and the type of the raw material gas.

However, from the viewpoint of obtaining a higher bubble growth-suppressing effect and a higher defoaming effect, it is preferable that the chains 21 of the internal 50 have the following configurations. For example, the length of a single chain 21 is preferably a length which allows the chain 21 to extend to the vicinity of the bottom of the body 10. Moreover, for example, it is preferable that each part constituting the chain 21 be finer. Furthermore, for example, it is preferable that parts constituting the chains 21 each have a projection. Use of the chains 21 employing at least one of the above configurations makes it possible to have a higher bubble growth-suppressing effect and a higher defoaming effect.

On the other hand, from the viewpoint of preventing entanglement of the chains 21, it is preferable that the chains 21 have the following configurations. For example, a single chain 21 is preferably thick. In a case where the chains 21 are thick, the chains 21 are restrained from swinging laterally. As a result, the chains 21 are hard to get entangled with each other. Moreover, for example, it is desirable that each part constituting the chains 21 each do not have a projection or the like which may cause entanglement of the chains 21.

The chains 21 may be made of a material such as nickel-alloy, stainless steel, steel stock, iron, or ceramics. More preferably, the chains 21 are made of a corrosion-resistant material. Use of the chains 21 which are corrosion-resistant makes it possible to reduce the frequency of replacement of the chains 21.

The internal 50 has two ends, one of which is an upper end attached to the cover 20 and the other one of which is a lower end on an opposite side of the upper end. The upper end is referred to as a first end, and the lower end is referred to as a second end. The first end is detachably attached to the cover 20. The first end is attached to the cover 20 by any method. For example, it is convenient for a worker if it is possible to attach/detach the plurality of chains 21 (preferably all of the chains 21) together to/from the cover 20.

Preferably, the second end is configured to be freely swingable within the fluidized bed reaction device 1. This is because the bubble growth-suppressing effect and the defoaming effect are enhanced if the second end swings inside the fluidized bed reaction device 1.

Figure 3B:
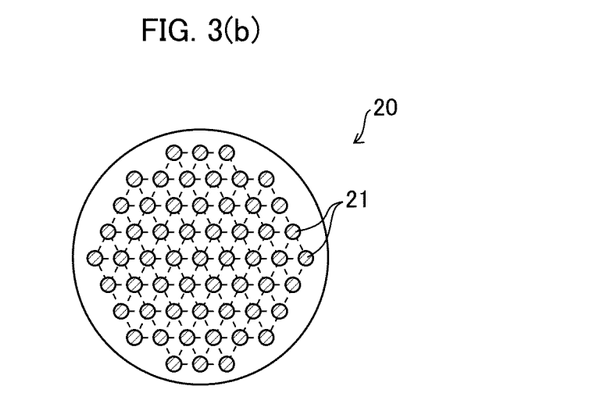

Next, the following will discuss, with reference to FIG. 3(b), a preferred installation density of the chains 21. FIG. 3(b) is a view illustrating an example arrangement of the chains 21 when the cover 20 is viewed from above. In FIG. 3(b), each circle represents a single chain 21. Note that dotted lines in FIG. 3(b) are imaginary lines for easier understanding of the arrangement of the chains 21, and in reality, no such lines exist.

It is preferable to have a larger number of chains per unit area. Moreover, it is preferable that the chains 21 be arranged so densely that the chains 21 cover an entire cross section of the body 10. Specifically, the number of the chains 21 per unit area is preferably 50 or more chains per square meter in the cross section of the body 10. Furthermore, the number of the chains 21 per unit area in the cross section of the body 10 is more preferably 60 or more chains per square meter. The upper limit of the number of the chains 21 per unit area is set as appropriate in accordance with the thickness of the chains. For example, the upper limit of the number of the chains 21 per unit area may be approximately 100 chains per square meter.

Further, in the fluidized bed reaction device 1 provided with the internal, it is possible to set, as appropriate, a ratio of an area occupied by the chains 21 to a cross-sectional area of the fluidized bed reaction device 1. Such a ratio may be set in accordance with the number and the thickness of the chains 21. It is alternatively possible to set in advance the ratio of the area occupied by the chains 21, and then to select the number and the thickness of the chains 21 so that the occupied area will be satisfied.

For example, the number and the thickness of the chains 21 may be appropriately selected so that the chains 21 will be provided so as to occupy an area of about 10% to 90% (more preferably, about 40% to 80%) of the cross-sectional area of the fluidized bed reaction device 1.

The gas bubbles become finer or are destroyed when the gas bubbles come in contact with the chains 21. However, in gaps between the chains 21, the gas bubbles do not come in contact with the chains 21. This results in a lower bubble growth-suppressing effect and a lower defoaming effect. Accordingly, it is possible to enhance the bubble growth-suppressing effect and the defoaming effect, by increasing the number of the chains 21 per unit area and decreasing the gaps. In addition, it is possible to enhance the bubble growth-suppressing effect and the defoaming effect, by minimizing a space where the chains 21 are absent in the body 10.

Further, it is preferable that the chains 21 be attached to the cover 20 at substantially constant intervals so as to be provided substantially uniformly in an inside space of the body 10. This is because the chains 21 as the internal also function to (1) improve contacting efficiency between the first material and the second material and (2) facilitate circulation of the second material inside the body 10.

[Defoaming Mechanism]

Figure 1:
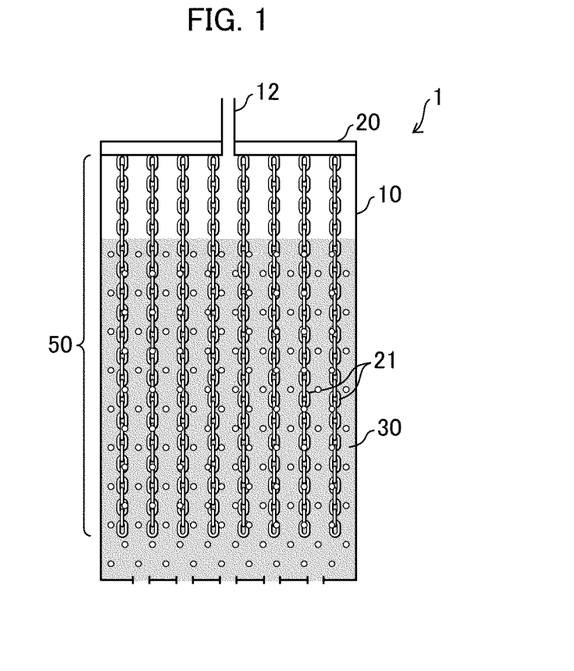
FIG. 1 is a cross-sectional view of a fluidized bed reaction device in accordance with an embodiment of the present invention.

Next, the following will discuss, with reference to FIG. 1, a mechanism by which the bubble growth-suppressing effect and the defoaming effect are obtained with use of the internal 50 in the fluidized bed reaction device 1. FIG. 1 is a cross-sectional view of the fluidized bed reaction device 1. Note that members having the same functions as those described in FIGS. 2, 3(a), and 3(b) are denoted by the same reference numerals, respectively, and descriptions thereof are omitted.

As illustrated in FIG. 1, the internal 50 is attached to the cover 20. The internal 50 has the plurality of chains 21. The chains 21 are densely arranged such that no large gap is formed between chains 21. Further, the body 10 is filled with the catalyst 30 (the second material). The catalyst 30 is, for example, a metal powder.

When the fluidized bed reaction device 1 starts operating, the first material (gases) is introduced into the body 10 through the plurality of inlet tubes 11. Each of the gases, which have been introduced, pass through a layer of the catalyst 30 (the catalytic bed, that is, fluidized bed). As the gases having been introduced pass through the catalytic bed, the gases each come in contact with the catalyst and another type of gas, and cause a reaction. The gases which have passed through the catalytic bed (and which also includes a newly generated gas) are collected through the outlet tube 12.

Here, when the gases having been introduced pass through the catalytic bed, large and small gas bubbles may be generated. In a case where the internal 50 is not attached to the fluidized bed reaction device 1, the gas bubbles thus generated may rise toward an interfacial surface while being combined with another gas bubble(s) to grow larger. Therefore, there may be a case where the contacting efficiency between the gases and the catalyst lowers and a yield resulting from the gas phase reaction decreases.

In contrast, in a case where the internal 50 is attached to the fluidized bed reaction device 1, the gas bubbles generated come in contact with the chains 21 while rising toward the interfacial surface. The gas bubbles are finely broken up when the gas bubbles come in contact with the chains 21. Further, when the gas bubbles come in contact with the chains 21, the chains 21 swing. This causes a change in flow of the catalytic bed, so that the gas bubbles which are not in direct contact with the chains 21 can also be finely broken up.

Further, the gas bubbles cannot grow to a size equal to or larger than the intervals at which the chains are provided. Therefore, dense arrangement of the chains 21 in the internal 50 makes it possible to suppress growth of the gas bubbles inside the body 10.

As described above, the fluidized bed reaction device 1 satisfactorily yields the bubble growth-suppressing effect and the defoaming effect, by including any of various types of the internal 50 described in the present embodiment. Therefore, the contacting efficiency between the raw material gases and the catalyst 30 is improved. This consequently increases the yield of the resultant product of the chemical reaction. Further, since the contacting efficiency between the raw material gases and the catalyst 30 is improved, it is possible to reduce an unreacted substance or an impurity (tar or the like) resulting from an incomplete reaction. Furthermore, the above reduction of the unreacted material and the impurity can lead to reduction of labor for recycling such substances. Therefore, it is also possible to save labor associated with both a preceding process and a subsequent process of the chemical reaction using the fluidized bed reaction device 1.

Further, the fluidized bed reaction device 1 can also promote flow of the catalytic bed, by including any of the various types of the internal 50 described in the present embodiment. Thus, for example, in a case where the catalyst is solid, the contacting efficiency between the raw material gases and the catalyst 30 is improved since the catalyst is micronized. Furthermore, it is possible to reduce an unreacted substance or an impurity (tar or the like) resulting from an incomplete reaction as the contacting efficiency between the raw material gases and the catalyst 30 is improved. This makes it possible to reduce clogging which may occur, due to generation of the impurity, in a pipe inside the body 10, such as the inlet tubes 11.

As illustrated in FIG. 1, it is preferable that the chains 21 extend to the vicinity of the bottom of the body 10 (the vicinity of the inlet tubes 11). This is because the gas bubbles are destroyed before they grow large. However, it is preferable that the chains 21 have a length which does not allow the chains 21 to hit the inlet tubes 11 or the bottom of the body 10. This is because when the chains 21 contact the inlet tubes 11 or the bottom of the body 10, the chains 21 are restrained from swinging. This consequently lowers the bubble growth-suppressing effect and the defoaming effect.

[Variations of Internal]

Next, the following will discuss variations of the internal, with reference to FIG. 4. For convenience of explanation, the term "first end" refers to one of two ends of the internal 50, which end is attached to the cover 20, and the term "second end" refers to the other one of the two ends of the internal 50, which end is on an opposite side of the first end. FIGS. 4(a) to 4(d) each illustrate another example of the internal 50.

Figure 4A:
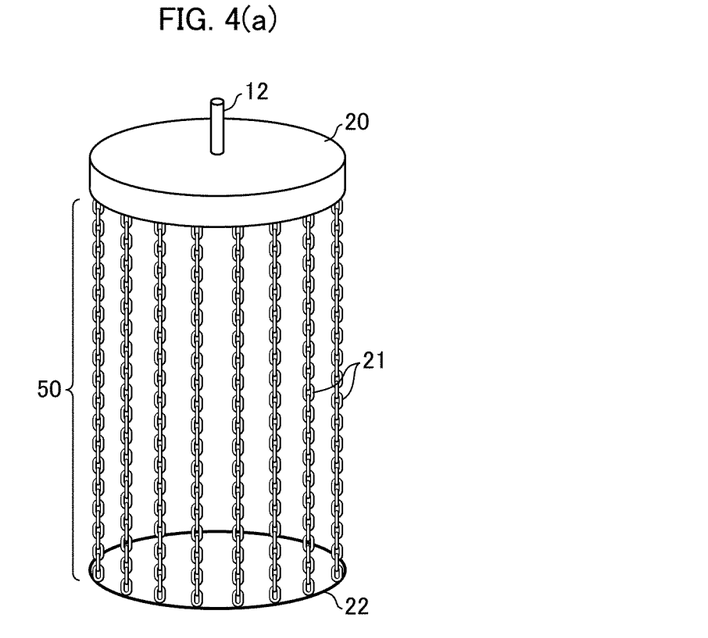

FIG. 4(a) is a view illustrating an internal 50 in which the chains 21 are connected to each other at the second end. As illustrated in FIG. 4(a), two or more of the chains 21 (preferably, all of the chains 21) may have respective second-end-side ends connected to each other via a connecting part 22. This makes it possible to prevent entanglement of the chains 21. As a result, the internal 50 can retain its function as an internal for a long period of time. For example, the internal 50 can efficiently function to:

(1) suppress growth of gas bubbles;
(2) destroy the gas bubbles;
(3) improve contacting efficiency between gas and particles; and
(4) facilitate circulation of the particles within the reaction device.

The connecting part 22 may be made of a material such as nickel-alloy, stainless steel, steel stock, iron, or ceramics. Use of the connecting part 22, which is corrosion-resistant, improves durability of the connecting part 22. As a result, the internal 50 can be used for a long period of time. The connecting part 22 may be connected with the chains 21 by any method. This also applies to the connecting part 22 described below with reference to each of FIGS. 4(b) and 4(c).

Figure 4B:
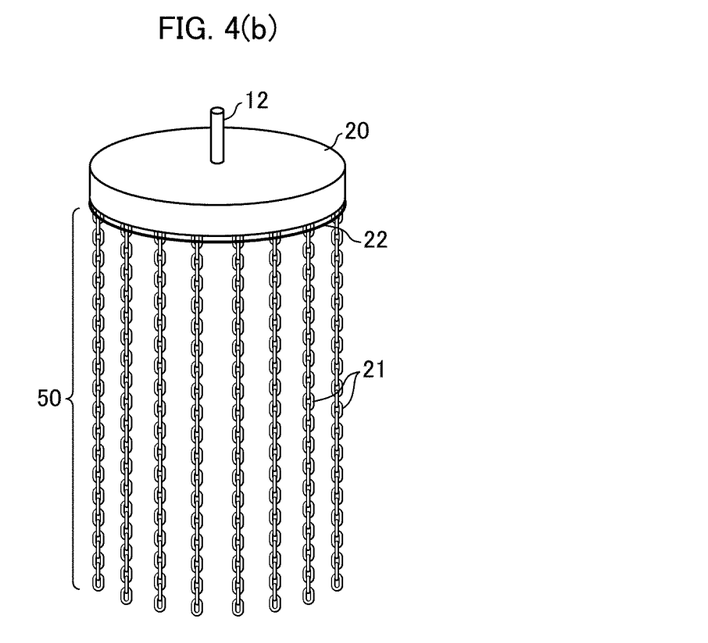

FIG. 4(b) is a view illustrating an internal 50 in which the chains 21 are connected to each other at the first end. As illustrated in FIG. 4(b), two or more of the chains 21 (preferably, all of the chains 21) may have respective first-end-side ends connected to each other via the connecting part 22.

This makes it easy to attach the internal 50 to the cover 20 because it is possible to prevent entanglement of the chains 21 on a first end side. As a result, the internal 50 can be more easily handled. Further, the cover 20 may include a first adapter (not illustrated), the connecting part 22 may include a second adapter (not illustrated), and the first adapter and the second adapter may be connected to each other by a single touch. This makes handling of the internal 50 even easier, since the cover 20 and the connecting part 22 are more easily connected to each other. Note that the first adapter and the second adapter are not particularly limited in structure.

Figure 4C:
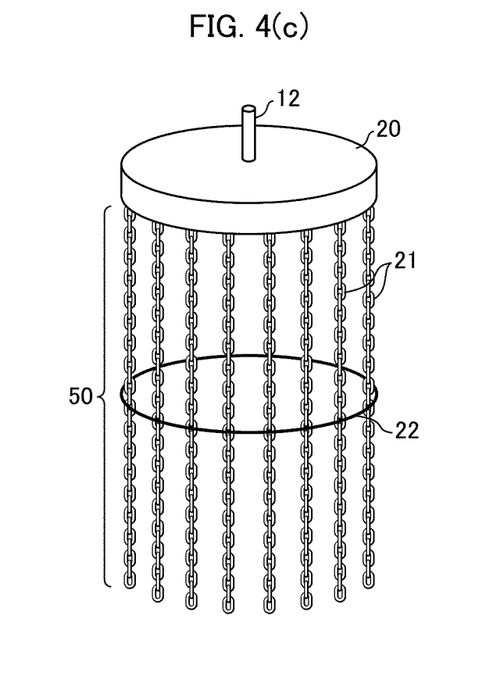
FIG. 4(c) is a view illustrating an internal in which chains are connected to each other between a first end and a second end.

FIG. 4(c) is a view illustrating an internal 50 in which the chains 21 are connected to each other between the first end and the second end. As illustrated in FIG. 4(c), two or more of the chains 21 (preferably, all of the chains 21) may be connected to each other via the connecting part 22 between the first end and the second end. This makes it possible to prevent entanglement of the chains 21. Further, in the internal 50 illustrated in FIG. 4(c), the second-end-side ends of the chains 21 are free ends which are not connected to each other. Therefore, the second-end-side ends of the chains 21 in FIG. 4(c) can easily swing. Therefore, in the internal 50 illustrated in FIG. 4(c), it is possible to not only prevent entanglement of the chains 21 but also expect a satisfactory bubble growth-suppressing effect and a satisfactory defoaming effect. Note that it is preferable that as illustrated in FIG. 4(c), the connecting part 22 be provided in the vicinity of the middle between the first-end-side ends and the second-end-side ends of the chains 21. This makes it possible to obtain, in a well-balanced manner, an effect of preventing entanglement of the chains 21 and the bubble growth-suppressing effect and the defoaming effect.

Figure 4D:
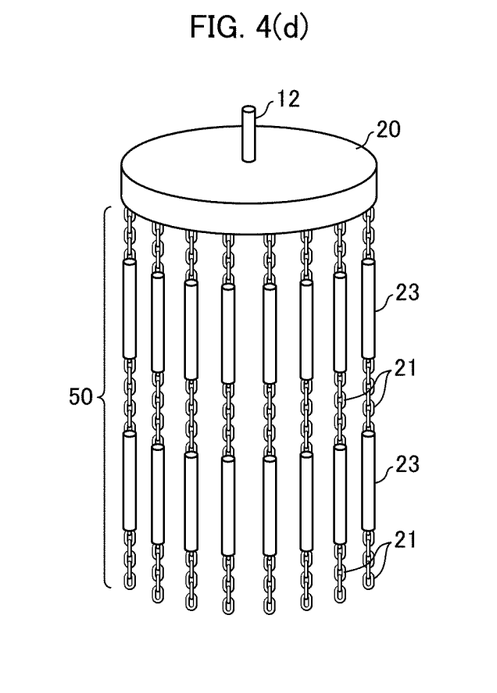
FIG. 4(d) is a view illustrating an internal including chains 21 and non-chain parts 23.

FIG. 4(d) is a view illustrating an internal including chains 21 and non-chain parts 23. Generally, since chains are light, foldable, and the like, chains are more easily handled as compared to bars or the like if the bars or the like are made of the same material and has the same size as the chains. Therefore, the internal 50 including the chains 21 illustrated in FIG. 4(d) is easily handled by a user.

It was also found that as described above, it is possible to obtain, by the internal 50 using the chains 21, a high defoaming effect in addition to improved contacting efficiency between the gas and the catalyst 30 and facilitated circulation of the particles inside the fluidized bed reaction device 1.

On the other hand, the internal 50 illustrated in FIG. 4(d) further includes the non-chain parts 23. The non-chain parts 23 are each made of, for example, a vertical pipe, a flat plate, a coil, a pipe, a plate, a tube, or a metallic rod. This makes it possible to provide various internals 50 which may vary from each other in terms of the defoaming effect, usability, cost, design, material, or the like. In a case where the non-chain parts 23 have a shape of any of the above-described examples, the non-chain parts 23 have an advantage of being hard to get entangled with each other. Therefore, the internal 50 including the chains 21 and the non-chain parts 23 has an advantage of being hard to get entangled with each other.

Application Examples

The fluidized bed reaction device 1 can be suitably used for producing a trifluoromethyl pyridine in which a part of a pyridine ring is substituted with a halogen (halogen-substituted trifluoromethyl pyridine). The following will discuss an example in which the fluidized bed reaction device 1 in accordance with the present embodiment is applied to production of a halogen-substituted trifluoromethyl pyridine.

The halogen-substituted trifluoromethyl pyridine is not particularly limited in position(s) and the number of position (s) substituted with a halogen in a pyridine ring, in a molecular structure of the halogen-substituted trifluoromethyl pyridine. For example, the fluidized bed reaction device 1 in accordance with the present embodiment can be suitably applied to production of a trifluoromethyl pyridine in which an atom or a molecule at a single position of the pyridine ring is substituted with a halogen (e.g., chlorotrifluoromethyl pyridines in a case where the halogen is a chlorine atom: CTFs). Moreover, the fluidized bed reaction device 1 in accordance with the present embodiment can be suitably applied to production of a trifluoromethyl pyridine in which atoms or molecules at two or more positions of the pyridine ring are substituted with halogens, respectively (e.g., dichlorotrifluoromethyl pyridines in a case where the two halogens are chlorine atoms: DCTFs).

The following will discuss respective examples in which the fluidized bed reaction device 1 in accordance with the present embodiment is applied to the production of CTFs and DCTFs.

[Production of CTFs]

In a case where a CTF is produced, raw materials (first material) are a pyridine-based compound such as a β-picoline, and a halogen (e.g., chlorine and hydrogen fluoride). On the other hand, the catalyst (second material) can be a metal powder made of, for example, aluminum, chromium, iron, or nickel, or a fluoride of any of these metals, activated carbon, or activated alumina. The fluidized bed reaction device 1 introduces a β-picoline, chlorine, and hydrogen fluoride through the inlet tubes 11, respectively, and causes a gas phase reaction of these introduced substances in the catalytic bed in the presence of the catalyst. Note that the chlorine and the hydrogen fluoride may be mixed in advance and then introduced. When the β-picoline reacts with the halogen, the inside of the body 10 is heated to 300° C. to 600° C. by the heater 13 or the like. The raw material gases stay in the body 10 for about 3 seconds to 60 seconds, so that a reaction occurs. As a result, gases containing the CTF can be collected from the outlet tube 12 as a resultant product. The gases, which have been thus collected and contain the CTF, are cooled in a subsequent process, and the CTF in the form of liquid is separated and collected.

Note that the above described production method is a method of producing chloro β-trifluoromethyl pyridine. However, the trifluoromethyl pyridine may have a $CF_3$ group at any of positions α, β, and γ of the pyridine ring. In addition, the number of positions substituted with the halogen in the pyridine ring of the trifluoromethyl pyridine may be 1 or more, and the positions substituted with the halogen in the pyridine ring may be at any positions.

[Production of DCTFs]

In a case where a DCTF is produced, an example of raw materials (first material) includes a CTF and chlorine. On the other hand, the catalyst (second material) can be a metal powder made of zinc, iron, cobalt, nickel, or antimony, or a chloride of any of these metals, or activated carbon. The fluidized bed reaction device 1 introduces the CTF and chlorine through the inlet tubes 11, respectively, and causes a gas phase reaction of these introduced substances in the catalytic bed in the presence of the catalyst. Note that during this reaction, the inside of the body 10 is heated to 200° C. to 400° C. by the heater 13 or the like. As a resultant product, the DCTF can be collected from the outlet tube 12.

Note that in a case where any of CTFs and DCTFs is produced, it is preferable that the raw material gases or the catalyst introduced have been heated to an appropriate temperature and activated in advance.

In a case where any of CTFs and DCTFs is produced, it is preferable that one or more of the plurality of inlet tubes 11 (e.g., inlet tubes 11 for introducing the β-picoline, hydrogen fluoride, chlorine, and an inert gas, respectively) of the fluidized bed reaction device 1 have a nozzle opening(s) which faces/face the bottom of the body 10. This makes it possible to reduce the size of bubbles generated at the time when the raw material gases are introduced.

In addition, when any of CTFs and DCTFs is produced, an inert diluent (e.g., argon, nitrogen helium or the like) may be added, in addition to the raw material gases and the catalyst. The inert diluent may be introduced through one of the inlet tubes 11 or may be added to the body 10 in advance prior to causing the reaction.

In this way, it is possible to use the fluidized bed reaction device 1 in accordance with the present embodiment in production of CTFs and DCTFs. Thus, it is possible to expect effects such as the above-described effects, that is, a promoted chemical reaction, an improved yield of a product resulting from the reaction, and the like.

Aspects of the present invention can also be expressed as follows:

An internal in accordance with Aspect 1 of the present invention is an internal for use in a fluidized bed reaction device in which a first material and a second material different from the first material are brought into contact with each other and reacted with each other, the internal including a plurality of chains and being attached to a ceiling part of the fluidized bed reaction device.

With the above configuration, the internal includes a plurality of chains. Since chains are easy to handle, the internal is easily handled. Further, the internal is attached to the ceiling part of the fluidized bed reaction device. The ceiling part is a place where workers can easily work. This makes handling of the internal (in particular, replacement work etc.) easier.

Moreover, in a case where chains are used as the internal, it is possible to obtain a defoaming effect, in addition to improved contacting efficiency between the first material and the second material and facilitated circulation of the second material inside the reaction device.

Therefore, the above configuration can provide an internal which is easily handled and which makes it possible to obtain a satisfactory defoaming effect.

The internal in accordance with Aspect 2 of the present invention may be configured to further include, in the above-described Aspect 1, a connecting part which connects two or more of the plurality of chains.

In the above configuration, the plurality of chains are hard to get entangled with each other. This allows the internal to retain its function as an internal for a long period of time.

An internal in accordance with Aspect 3 of the present invention may be configured such that, in the above-described Aspect 2, on the assumption that the internal has two ends one of which is attached to the ceiling part and referred to as a first end and the other one of which is on an opposite side of the first end and referred to as a second end, the connecting part is connected, at the second end, with two or more of the plurality of chains.

In the above configuration, the plurality of chains are harder to get entangled with each other. This allows the internal to retain its function as an internal for a longer period of time. At the same time, it is possible to obtain a defoaming effect since the plurality of chains swing within the fluidized bed reaction device.

An internal in accordance with Aspect 4 of the present invention may be configured such that, in the above-described Aspect 2, on the assumption that the internal has two ends one of which is attached to the ceiling part and referred to as a first end and the other one of which is on an opposite side of the first end and referred to as a second end, the connecting part is connected, at the first end, with each of the plurality of chains, and also with the ceiling part.

In the above configuration, the internal is easily attached to the ceiling part because it is possible to prevent entanglement of the plurality of chains on a first end side. This makes handling of the internal even easier.

An internal in accordance with Aspect 5 of the present invention may be configured such that, in the above-described Aspect 2, on the assumption that the internal has two ends one of which is attached to the ceiling part and referred to as a first end and the other one of which is on an opposite side of the first end and referred to as a second end, the connecting part is connected, between the first end and the second end, with two or more of the plurality of chains.

In the above configuration, the plurality of chains are hard to get entangled with each other. At the same time, it is possible to obtain a defoaming effect since the plurality of chains swing within the fluidized bed reaction device.

The internal in accordance with Aspect 6 of the present invention may be configured such that, in any one of the above-described Aspects 1 to 5, the internal is detachably attached to the ceiling part.

The above configuration makes it easy to, for example, replace, repair, or check the internal. This makes handling of the internal even easier.

A fluidized bed reaction device in accordance with Aspect 7 of the present invention is a fluidized bed reaction device configured to include: a body filled with a second material; one or more inlet tubes for introducing, into the body, a first material which chemically reacts with the second material when brought into contact with the second material; and an internal including one or more chains which are hung inside the body.

The above configuration yields the same effect as the internal described above.

A fluidized bed reaction device in accordance with Aspect 8 of the present invention may be configured such that, in the above-described Aspect 7, in a case where the internal includes a plurality of chains, the plurality of chains are arranged at substantially equal intervals.

The above configuration allows the internal to efficiently function to (1) suppress growth of gas bubbles, (2) destroy the gas bubbles, (3) improve contacting efficiency between gas and particles; and (4) facilitate circulation of the particles within the reaction device. Further, since the plurality of chains are arranged at substantially constant intervals, the plurality of chains are hard to get entangled with each other. This improves usability.

Therefore, the fluidized bed reaction device benefits from the effect obtained by the internal.

A fluidized bed reaction device in accordance with Aspect 9 of the present invention may be configured such that, in the above-described Aspect 8, the plurality of chains are provided such that 50 or more chains per square meter are present in a cross section of the body.

The above configuration makes it possible to provide a fluidized bed reaction device excellent in defoaming effect of the internal.

An fluidized bed reaction device in accordance with Aspect 10 of the present invention may be configured such that, in any one of the above-described Aspects 7 to 9, the internal has a first end attached to a ceiling part of the fluidized bed reaction device, and a second end being on an opposite side of the first end and configured so as to be swingable inside the body.

The above configuration allows the internal to be easily attached to the ceiling part. This makes handling of the internal easier. Further, the above configuration ensures the defoaming effect of the internal, since the chains are swingable on a second end side. Accordingly, the above configuration makes it possible to provide a fluidized bed reaction device including an internal which has a satisfactory defoaming effect and which is easily handled.

A fluidized bed reaction device in accordance with Aspect 11 of the present invention may be configured to further include, in any one of the above-described Aspects 7 to 10, a connecting part which connects with two or more of a plurality of chains in a case where the internal includes the plurality of chains.

The above configuration yields the same effect as the internal described above.

An fluidized bed reaction device in accordance with Aspect 12 of the present invention may be configured such that, in the above-described Aspect 11: the internal has a first end attached to the ceiling part of the fluidized bed reaction device; and the connecting part connects with two or more of the plurality of chains, on a second end side opposite to the first end.

The above configuration yields the same effect as the internal described above.

A fluidized bed reaction device in accordance with Aspect 13 of the present invention may be configured such that, in any one of the above-described Aspects 7 to 12, the one or more inlet tubes are connected to a bottom of the body.

In the above configuration, the first material is introduced into the body from the bottom of the body. In a case where the first material is gas, the first material flows from the bottom of the body to the ceiling part of the body. In this case, the body is filled with the second material.

Therefore, the above configuration makes it possible to cause the first material with the second material different from the first material to efficiently contact and react with each other.

A fluidized bed reaction device in accordance with Aspect 14 of the present invention may be configured such that: in the above-described Aspect 13, the one or more inlet tubes include a plurality of inlet tubes; and at least one of the one or more inlet tubes has a tip portion which projects into the body and which has an opening facing the bottom of the body.

The above configuration makes it possible to prevent the first material from being introduced in a state which may cause the first material to be non-uniformly mixed with the second material, in introducing the first material through any of the inlet tubes (e.g., prevent bubbles).

A fluidized bed reaction device in accordance with Aspect 15 of the present invention may be configured such that, in any one of the above-described Aspects 7 to 14, the internal includes chains and non-chain parts.

In the above configuration, the internal includes the chains. Since chains are easy to handle, the internal is easily handled. Moreover, in a case where chains are used as the internal, it is possible to obtain a defoaming effect, in addition to improved contacting efficiency between the first material and the second material and facilitated circulation of the second material inside the reaction device.

Further, in the above configuration, the internal also includes the non-chain parts. Accordingly, it is possible to provide various internals which may vary in terms of the defoaming effect, usability, cost, design, materials, or the like.

A method in accordance with Aspect 16 of the present invention of producing a halogen-substituted trifluoromethyl pyridine, the method comprising the step of: causing, by use of a fluidized bed reaction device described in any one of the above Aspects 7 to 15, a gas phase reaction of a pyridine-based compound and a halogen in presence of a catalyst, the pyridine-based compound and the halogen being the first material, the catalyst being the second material, the halogen-substituted trifluoromethyl pyridine being a trifluoromethyl pyridine in which a part of a pyridine ring is substituted by the halogen.

The above method makes it possible to improve a yield of the halogen-substituted trifluoromethyl pyridine.

A method in accordance with Aspect 17 of the present invention of producing a trifluoromethyl pyridine, the method comprising the step of: causing, by use of a fluidized bed reaction device described in any one of the above Aspects 7 to 15, a gas phase reaction of a halogen-substituted trifluoromethyl pyridine and a halogen in presence of a catalyst, the halogen-substituted trifluoromethyl pyridine and the halogen being the first material, the catalyst being the second material, the trifluoromethyl pyridine having parts of a pyridine ring substituted by at least two halogens.

The above method makes it possible to improve a yield of the trifluoromethyl pyridine in which substitution with at least two halogens has occurred.

The present invention is not limited to the embodiments, but can be altered by a skilled person in the art within the scope of the claims. The present invention also encompasses, in its technical scope, any embodiment derived by combining technical means disclosed in differing embodiments.

REFERENCE SIGNS LIST 1 fluidized bed reaction device
10 body
11 inlet tube
12 outlet tube
13 heater
21 chain
22 connecting part
23 non-chain part
30 catalyst
50 internal

The invention claimed is:

1. A fluidized bed reaction device, comprising:
a body filled with a second material;
one or more inlet tubes for introducing, into the body, a first material which chemically reacts in the presence of the second material when brought into contact with the second material; and
an internal including one or more chains which are hung inside the body, wherein, in a case where the internal includes a plurality of chains, the plurality of chains are arranged at substantially equal intervals and the plurality of chains are provided such that 50 or more chains per square meter are present in a cross section of the body.

2. The fluidized bed reaction device as set forth in claim 1, wherein the internal has a first end attached to a ceiling part of the fluidized bed reaction device, and a second end being on an opposite side of the first end and configured so as to be swingable inside the body.

3. The fluidized bed reaction device as set forth in claim 1, wherein the one or more inlet tubes are connected to a bottom of the body.

4. A method of producing a halogen-substituted trifluoromethyl pyridine, the method comprising the step of:
causing, by use of a fluidized bed reaction device, a gas phase reaction of a pyridine-based compound and a halogen in the presence of a catalyst, wherein the fluidized bed reaction device comprises a body filled with a second material; one or more inlet tubes for introducing, into the body, a first material which chemically reacts in the presence of the second material when brought into contact with the second material; and an internal including one or more chains which are hung inside the body,
the pyridine-based compound and the halogen being the first material,
the catalyst being the second material, and
the halogen-substituted trifluoromethyl pyridine being a trifluoromethyl pyridine which a part of a pyridine ring is substituted by the halogen.

5. A method of producing a trifluoromethyl pyridine, the method comprising the step of:
causing, by use of a fluidized bed reaction device, a gas phase reaction of a halogen-substituted trifluoromethyl pyridine and a halogen in the presence of a catalyst, wherein the fluidized bed reaction device comprises a body filled with a second material; one or more inlet tubes for introducing, into the body, a first material which chemically reacts in the presence of the second material when brought into contact with the second material; and an internal including one or more chains which are hung inside the body, the halogen-substituted trifluoromethyl pyridine and the halogen being the first material, the catalyst being the second material, and the trifluoromethyl pyridine having parts of a pyridine ring substituted by at least two halogens.

6. An internal for use in a fluidized bed reaction device in which a first material and a second material different from the first material are brought into contact with each other, the internal comprising a plurality of chains, which are attached to a ceiling part of the fluidized bed reaction device and a connecting part which connects two or more of the plurality of chains, wherein two or more of the plurality of chains are connected to each other via the connecting part at a second end of the internal.

7. An internal for use in a fluidized bed reaction device in which a first material and a second material different from the first material are brought into contact with each other, the internal comprising a plurality of chains, which are attached to a ceiling part of the fluidized bed reaction device and a connecting part which connects two or more of the plurality of chains, wherein two or more of the plurality of chains are connected to each other via the connecting part between a first end and a second end of the internal.

\* \* \* \* \*